United States Patent
Rasmussen et al.

(10) Patent No.: US 6,525,084 B2
(45) Date of Patent: *Feb. 25, 2003

(54) STABLE PHARMACEUTICAL FORMULATION

(75) Inventors: Stella Rudkjær Rasmussen, Copenhagen (DK); Per Grønlund, Hillerød (DK)

(73) Assignee: Novo Nordisk A/S, Bagsvaerd (DK)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 26 days.

(21) Appl. No.: 09/358,024

(22) Filed: Jul. 21, 1999

(65) Prior Publication Data

US 2002/0022649 A1 Feb. 21, 2002

Related U.S. Application Data

(60) Provisional application No. 60/094,343, filed on Jul. 28, 1998.

(30) Foreign Application Priority Data

Jul. 23, 1998 (DK) .................................. PA 1998 00970

(51) Int. Cl.[7] ..................... A61K 31/4025; A61K 9/16; C07D 405/08; C07D 405/12
(52) U.S. Cl. ..................... 514/422; 548/517; 424/465; 424/491
(58) Field of Search ..................... 514/422; 548/517; 424/465, 491

(56) References Cited

U.S. PATENT DOCUMENTS 5,407,955 A * 4/1995 Bryant et al.
5,464,862 A * 11/1995 Labroo et al.

OTHER PUBLICATIONS

Liu et al., Proceed Int'l. Symp. Control. Rel. Bioact. Mater., vol. 25, pp. 970–971 (1998) (Controlled Release Society, Inc.
Westerhius et al., International Journal of Pharmaceutics, vol. 156, pp. 109–117 (1997).
Schaefer et al., Pharm. Ind. vol. 52, No. 9, pp. 1147–1153 (1990).
Horsthuis et al., International Journal of Pharmaceutics, vol. 92, pp. 143–150 (1993).
Wehrle et al., Drug Development and Industrial Pharmacy, vol. 19, No. 13, pp. 1637–1653 (1993).

* cited by examiner

*Primary Examiner*—Taofiq Solola
(74) *Attorney, Agent, or Firm*—Reza Green

(57) ABSTRACT

This invention relates to a novel granulate and a novel oral solid dosage formulation, each comprising an active ingredient and one or more carriers prepared by a novel wet granulation method. This method provides that the mixture of active ingredient and carrier be kept below 40° C. during the granulation process such that a more stable formulation is obtained.

10 Claims, No Drawings

STABLE PHARMACEUTICAL FORMULATION

CROSS-REFERENCE TO RELATED APPLICATIONS

This application claims priority under 35 U.S.C. 119 of U.S. provisional application No. 60/094,343 filed Jul. 28, 1998 and Danish application no. 1998 00970 filed Jul. 23, 1998, the contents of which are fully incorporated herein by reference.

FIELD OF THE INVENTION

This invention relates to a novel granulate and a novel oral solid dosage formulation comprising an active ingredient and one or more carriers. Moreover the invention relates to a wet granulation method for preparing the granulate as well as a wet granulation method for preparing the oral solid dosage form.

BACKGROUND OF THE INVENTION

High shear mixers are widely used in the pharmaceutical industry for blending and granulation (cf. Handbook of pharmaceutical granulation technology, chapter 7, "Drugs and the pharmaceutical sciences", vol. 81, 1997). Blending and wet massing is accomplished by high mechanical agitation by an impellar and chopper. High shear mixers have applications other than wet granulation, as it can be used for melt granulation and pelletization. When melt granulation or pelletization is performed, energy for melting the binder is supplied by agitation of the impellar and external heating of the bowl.

Compounds of Formula I

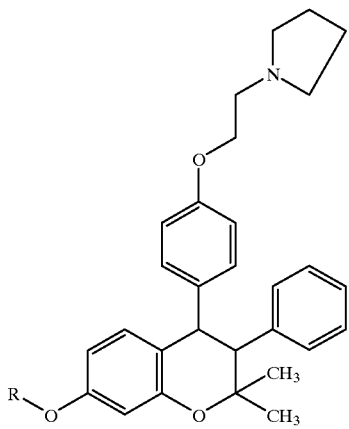

(I)

wherein R is hydrogen or $C_{1-6}$alkyl; or a pharmaceutically acceptable salt thereof, are described in i.a. U.S. Pat. No. 5,280,040. This patent describes the preparation of these compounds, as well as their use for reducing or preventing bone loss. The preparation of pharmaceutical compositions is also described.

Centchroman, which is 3,4-trans-2,2-dimethyl-3-phenyl-4-[4-(2-pyrrolidin-1-yl)ethoxy)phenyl]-7-methoxychroman, is a non-steroidal compound known to have antiestrogenic activity. It is in use in India as an oral contraceptive (see, for example, Salman et al., U.S. Pat. No. 4,447,622; Singh et al., Acta Endocrinal (Copenh) 126 (1992), 444–450; Grubb, Curr Opin Obstet Gynecol 3 (1991), 491–495; Sankaran et al., Contraception 9 (1974), 279–289; Indian Patent Specification No. 129187). Centchroman has also been investigated as an anti-cancer agent for treatment of advanced breast cancer (Misra et al., Int J Cancer 43 (1989), 781–783. Recently, centchroman as a racemate has been found as a potent cholesterol lowering pharmaceutical agent expressed by a significant decrease of the serum concentrations (S. D. Bain et al., J Min Bon Res 9 (1994), S 394).

Levormeloxifene, (−)-3R,4R -trans-7-methoxy-2,2-dimethyl-3-phenyl4-{4-[2-(pyrrolidin-1-yl)ethoxy]phenyl}chromane, is a particular preferred compound from this series of 3,4-diarylchromans. Levormeloxifene may be used in human and veterinary medicine for the regulation of bone metabolism. It may be used, for example, in the treatment of patients suffering from bone loss due to osteoporosis (including post-menopausal osteoporosis and glucocorticoid-related osteoporosis), Paget's disease, hyperparathyroidism, hypercalcemia of malignancy and other conditions characterized by excessive rates of bone resorption and/or decreased rates of bone formation.

The 3,4-diarylchromans are prepared according to known methods, such as those disclosed in U.S. Pat. No. 3,340,276 to Carney et al., U.S. Pat. No. 3,822,287 to Bolger, and Ray et al., J Med Chem 19 (1976), 276–279, the contents of which are incorporated herein by reference. Conversion of the cis isomer to the trans configuration by means of an organometallic base-catalyzed rearrangement is disclosed in U.S. Pat. No. 3,822,287. The optically active d- and l-enantiomers may be prepared as disclosed by Salman et al. in U.S. Pat. No. 4,447,622 (incorporated herein by reference) by forming an optically active acid salt which is subjected to alkaline hydrolysis to produce the desired enantiomer. The resolution of (±)-3,4-trans-7-methoxy-2,2-dimethyl-3-phenyl-4-{4-[2-(pyrrolidin-1-yl)ethoxy]phenyl}chromane in its optical antipodes is described in U.S. Pat. No. 4,447,622 incorporated herein by reference. Example 1 of U.S. Pat. No. 4,447,622 describes the preparation of the minus enantiomer, shown by formula II:

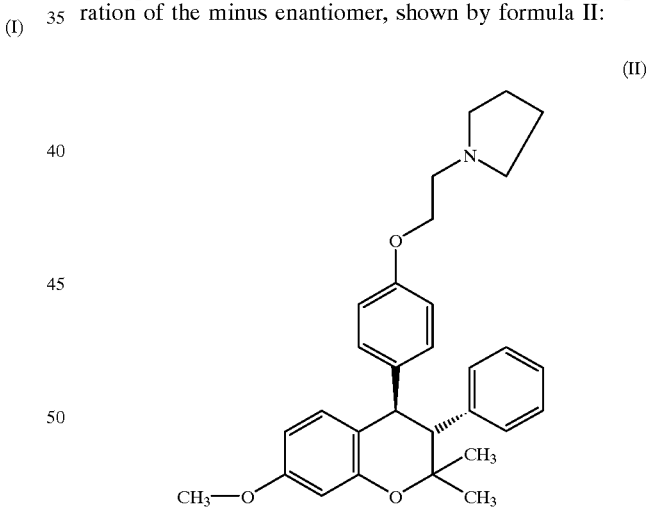

(II)

(In this specification, the compound of formula II is referred to as levormeloxifene.) In example 2 of U.S. Pat. No. 4,447,622, levormeloxifene is obtained as the free base and the hydrochloride salt.

The compounds of formula I may be administered as pharmaceutically acceptable salts. A particularly useful pharmaceutically acceptable salt of levormeloxifene is the hydrogen fumarate salt. This salt form is prepared by dissolving fumaric acid and (−)-3R,4R-trans-7-methoxy-2,2-dimethyl-3-phenyl-4-{4-[2-(pyrrolidin-1-yl)ethoxy]phenyl}chromane in a common solvent such as e.g. methanol, and crystallizing the resulting salt from the solution.

Tiagabine is disclosed in U.S. Pat. No. 5,010,090 incorporated herein by reference. (2E)-5-amino-5-methylhex-2-enoic acid N-methyl-N-((1R)-1-(N-methyl-N-((1R)-1-(methylcarbamoyl)-2-phenylethyl)carbamoyl)-2-(2-naphthyl)ethyl)amide is disclosed in WO 97/23508 incorporated herein by reference. Raloxifene is disclosed in U.S. Pat. No. 4,418,068 and U.S. Pat. No. 4,133,814 incorporated herein by reference. Idoxifene is disclosed in EP 260066 B1 and U.S. Pat. No. 4,839,155 incorporated herein by reference. Tamoxifene is disclosed in U.S. Pat. No. 4,536,516 incorporated herein by reference. 4-hydroxy Tamoxifene is disclosed in U.S. Pat. No. 4,623,660 incorporated herein by reference. Toremifene is disclosed in U.S. Pat. No. 4,996,225 incorporated herein by reference. Droloxifene is disclosed in EP 792640 incorporated herein by reference.

An object of the present invention is to provide a novel granulate or oral solid dosage form with improved stability properties.

A further object of the present invention is to provide a novel tablet or capsule with possibility of extension of long term shelf-life.

Further objects of the present invention will become apparent from the specification.

Accordingly, the present invention relates to a wet granulation method for preparing a granulate comprising an active ingredient and one or more carriers, the method comprising a) formation of a mixture of the active ingredient and one or more carriers, b) granulation of the mixture and c) drying the mixture, wherein the granulation is performed in a high shear mixing means with a temperature regulating means for keeping the temperature below about 40° C. in the mixture during granulation.

In another aspect of the present invention the wet granulation method for preparing a granulate comprising an active ingredient and one or more carriers, further comprises processing the granulate into an oral solid dosage formulation. In other words the present invention relates to a wet granulation method for preparing an oral solid dosage formulation comprising an active ingredient and one or more carriers, the method comprising a) formation of a mixture of the active ingredient and one or more carriers, b) granulation of the mixture, c) drying the mixture, and d) processing the granulate into an oral solid dosage formulation, wherein the granulation is performed in a high shear mixing means with a temperature regulating means for keeping the temperature below about 40° C. in the mixture during granulation. In one embodiment the oral solid dosage formulation is a tablet.. In another embodiment the oral solid dosage formulation is a capsule. In a further embodiment the oral solid dosage formulation, such as tablet or capsule, is coated with a film.

In a further embodiment of the present method the temperature in the granulation mixture is lower than about 35° C. In a particular embodiment the temperature is from about 0° C. to about 35° C., more preferred from about 0° C. to about 30° C., even more preferred from about 0° C. to about 25° C., still even more preferred from about 15° C. to about 30° C., and most preferred from about 20° C. to about 25° C. In still further embodiments of the present method, which embodiments should be considered independently of each other, the temperature in the granulation mixture is from about −20° C. to about 40° C., from about −10° C. to about 40° C., from about −10° C. to about 0° C., from about 0° C. to about 10° C., from about 10° C. to about 20° C., from about 20° C. to about 30° C., from about 30° C. to about 40° C., from about 0° C. to about 40° C., from about 10° C. to about 35° C., from about 15° C. to about 25° C., or from about 20° C. to about 25° C.

In a further embodiment of the present method the active ingredient is selected from non-peptide organic molecules, small peptides and peptide mimetics. In one embodiment the active ingredient is a non-peptide organic molecule. In another embodiment the active ingredient is a small peptide. In a further embodiment the active ingredient is a peptide mimetic. In a further embodiment the active ingredient has a molecular weight of below 1500 daltons, such as from 200 to 1500 daltons, preferably from 500 to 1000 daltons.

In a further embodiment of the present method the active ingredient is selected from non-peptide organic molecules, small peptides and peptide mimetics, such as centchroman, levormeloxifene, tiagabine, (2E)-5-amino-5-methylhex-2-enoic acid N-methyl-N-((1R)-1-(N-methyl-N-((1R)-1-(methylcarbamoyl)-2-phenylethyl)carbamoyl)-2-(2-naphthyl)ethyl)amide, ipamorelin, raloxifene, idoxifene, tamoxifene and droloxifene or pharmaceutically acceptable salts thereof, each of which is considered to be an alternative embodiment. In a preferred embodiment the active ingredient is levormeloxifene or a pharmaceutically acceptable salt thereof, more preferred levormeloxifene hydrogen fumarate or levormeloxifene hydrogen maleate, most preferred levormeloxifene hydrogen fumarate.

In a still further embodiment of the present method the active ingredient is selected from a compound of formula I

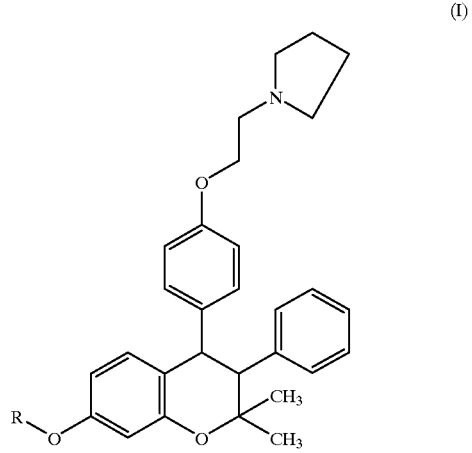

(I)

wherein R is hydrogen or $C_{1-6}$alkyl; or a pharmaceutically acceptable salt thereof. In one embodiment R is methyl. In another embodiment the compound of formula I is in the trans configuration. In a further embodiment the compound of formula I is 3,4-trans-2,2-dimethyl-3-phenyl-4-[4-(2-pyrrolidin-1-yl)ethoxy)phenyl]-7-methoxychroman (centchroman). In a still further embodiment the compound of formula I is an isolated I-enantiomer. In a further embodiment the compound of formula I is (−)-3R,4R-trans-7-methoxy-2,2-dimethyl-3-phenyl-4-{4-[2-(pyrrolidin-1-yl) ethoxy]phenyl}chromane (levormeloxifene). In a still further embodiment the compound of formula I is in the form of the hydrogen fumarate salt. In a further embodiment the compound of formula I is in the form of the hydrogen maleate salt.

The one or more carriers are such which are commonly used in the pharmaceutical chemistry for preparing granulates, see eg. Remington: The Science and Practice of Pharmacy, 19th Edition (1995) and/or Handbook of pharmaceutical granulation technology, chapter 7, "Drugs and the pharmaceutical sciences", vol. 81, 1997. In a further embodiment of the present method the one or more carriers are selected from hydrophilic binders, water-soluble diluents, surfactants, detergents, lubricants, disintegrants, antioxidants, non water-soluble diluents and/or other fillers known to the skilled person. In a particular embodiment the one or more carriers comprises at least a hydrophilic binder and a water-soluble diluent.

In a further aspect the present invention relates to a granulate comprising an active ingredient and one or more carriers, obtainable by the wet granulation method for preparing a granulate comprising an active ingredient and one or more carriers, the method comprising a) formation of a mixture of the active ingredient and one or more carriers, b) granulation of the mixture and c) drying the mixture, wherein the granulation is performed in a high shear mixing means with a temperature regulating means for keeping the temperature below about 40° C. in the mixture during granulation. In one embodiment the granulate is obtained by said method.

In a still further aspect the present invention relates to an oral solid dosage formulation comprising an active ingredient and one or more carriers, obtainable by the wet granulation method for preparing an oral solid dosage formulation comprising an active ingredient and one or more carriers, the method comprising a) formation of a mixture of the active ingredient and one or more carriers, b) granulation of the mixture, c) drying the mixture, and d) processing the granulate into an oral solid dosage formulation, wherein the granulation is performed in a high shear mixing means with a temperature regulating means for keeping the temperature below about 40° C. in the mixture during granulation. In one embodiment the oral solid dosage formulation is obtained by said method. In another embodiment the oral solid dosage formulation is a tablet or capsule, preferably a tablet. In a particular embodiment of the oral solid dosage formulation the preferred range of total mass may be from about 40 mg to about 500 mg depending on the strength of the formulation, more preferred from about 80 mg to about 320 mg, most preferred from about 80 mg to about 120 mg.

In a special aspect of the above methods, if the wet massing step is left out in the disclosed wet granulation method a stable powder (instead of a stable granulation) will be obtained, which powder may be used for administration to a patient, eg. in solution or suspension, or may be compressed into an oral solid dosage form, eg. tablets.

Oral solid dosage formulations or compositions containing an active ingredient, eg. a compound of formula I may be administered one or more times per day or week. An effective amount of such an active ingredient, eg. a compound of formula I is the amount required to effect prophylaxis or treatment of relevant disease-states. Such amount will depend, in part, on the particular disease-state and its severity, and age, weight, and general health of the patient, and other factors evident to those skilled in the art, but can be determined routinely by one of ordinary skill in the art having regard to his own knowledge. A typical daily dose will contain a nontoxic dosage range of from about 0.0001 to about 75 mg/kg patient per day of an active ingredient, eg. a compound of formula I, in particular levormeloxifene. A suitable dose of a compound of formula I, such as levormeloxifene, is e.g. from 0.01 to 2.5 mg per day to a patient, eg. a woman.

DEFINITIONS

As used herein, the term "$C_{1-6}$alkyl" includes straight and branched chain alkyl radicals containing from 1 to 6 carbon atoms, such as methyl, ethyl, n-propyl, isopropyl, n-butyl, tert-butyl, n-amyl, sec-amyl, n-hexyl, 2-ethylbutyl, 2,3-dimethylbutyl and the like.

The term "a wet granulation method" represents a conventional way of making granules and is disclosed in eg. Remington: The Science and Practice of Pharmacy, 19th Edition (1995) and/or in Handbook of pharmaceutical granulation technology, chapter 7, "Drugs and the pharmaceutical sciences", vol. 81, 1997. The wet method usually comprises the steps of weighing, mixing, granulation, screening the damp mass, drying, and optionally dry screening, lubrication and compression.

The term "a granulate" is intended to mean the granulate obtainable by using the wet granulation method and has the general meaning as disclosed in eg. Remington: The Science and Practice of Pharmacy, 19th Edition (1995) and/or in Handbook of pharmaceutical granulation technology, chapter 7, "Drugs and the pharmaceutical sciences", vol. 81, 1997. The granules may have any suitable size, depending on the carriers and/or equipment used and the preparation of granules with a particular size and structure is within the technical knowledge of the skilled person.

The term "an active ingredient" is intended to mean any compound having a therapeutic effect, and which is suitable for administration as an oral solid dosage formulation, such as non-peptide organic molecules, small peptides and peptide mimetics, and the like, as well as their pharmaceutically acceptable salts, in particular, but not limited to, a compound of formula I eg. centchroman or levormeloxifene; tiagabine, (2E)-5-amino-5-methylhex-2-enoic acid N-methyl-N-((1R)-1-(N-methyl-N-((1R)-1-(methylcarbamoyl)-2-phenylethyl) carbamoyl)-2-(2-naphthyl)ethyl)amide, ipamorelin, raloxifene, idoxifene, tamoxifene, 4-hydroxy tamoxifene, toremifene, or droloxifene or pharmaceutically acceptable salts thereof. The active ingredient itself may be stable upon storage or under stress conditions, but when formulated with one or more carriers it shows stability problems, eg. it starts to degrade.

The term "one or more carriers" is intended to mean such carriers which are commonly used in the pharmaceutical chemistry for preparing granulates and oral solid dosage formulations, see eg. Remington: The Science and Practice of Pharmacy, 19th Edition (1995) and/or Handbook of pharmaceutical granulation technology, chapter 7, "Drugs and the pharmaceutical sciences", vol. 81, 1997. In particular such one or more carriers are selected from, but not limited to, hydrophilic binders, water-soluble diluents, surfactants, lubricants, disintegrants, antioxidants, non water-soluble diluents and/or other fillers known to the skilled person.

The term "formation of a mixture of the active ingredient and one or more carriers" is intended to have its usual meaning, ie. mixing the active ingredient and carriers, in a suitable container, so as to form a mixture. For instance, the container may be the high shear mixing means wherein the granulation of the mixture takes place, but it is not limited hereto.

The term "granulation of the mixture" is intended to have its usual meaning, as disclosed in eg. Remington: The Science and Practice of Pharmacy, 19th Edition (1995) or in Handbook of pharmaceutical granulation technology, chapter 7, "Drugs and the pharmaceutical sciences", vol. 81, 1997; and include one or more of dry blending, wet massing, and after granulation.

The term "drying the mixture" is intended to have its usual meaning, as disclosed in eg. Remington: The Science and Practice of Pharmacy, 19th Edition (1995) or in Handbook of pharmaceutical granulation technology, chapter 7, "Drugs and the pharmaceutical sciences", vol. 81, 1997; and comprises drying the granulation mixture in a conventional manner either inside or outside the high shear mixing means, such as, but is not limited to, by placing the moist granulation mixture in drying cabinets with circulating air current and thermostatic heat control.

The term "a high shear mixing means" is intended to mean a high shear mixer, high speed mixer or high shear granulator or similar mixer/granulator as disclosed in eg. Remington: The Science and Practice of Pharmacy, 19th Edition (1995) or in Handbook of pharmaceutical granulation technology, chapter 7, "Drugs and the pharmaceutical sciences", vol. 81, 1997; and comprises, but is not limited to, a high shear mixer, such as a high speed, high shear mixer, such as a vertical axis high shear mixer or a horisontal axis high shear mixer. The high shear mixer may be selected from the following types: Gral, Lodige/Littleford, Diosna, Fielder or Baker-Perkins.

The term "a temperature regulating means" is intended to comprise any such means that can increase or lower the temperature in a mixture, eg. contained in a high shear mixing means. Such temperature regulating means comprises, but is not limited to, internal or external temperature regulating means, such as an internal or external cooling mantle with a fluid such as cold water (4–5° C.), or internal cooling tubes, or dry ice added in the high shear mixing means, or the high shear mixing means may be placed in a larger container which operates as a freezer.

The term "a high shear mixing means with a temperature regulating means" is intended to mean that the high shear mixing means is either equiped with the temperature regulating means, which may constitute an integrated part thereof, or the temperature regulating means may be separate from the high shear mixing means and still regulate temperature, for instance if the high shear mixing means is placed in a larger container which operates as a freezer.

The term "during granulation" is intended to mean during the entire granulation period, or during a part or parts of the granulation period, such as, but not limited to, during wet massing.

The term "processing the granulate" is intended to mean the further conventional processing of the granulate into an oral solid dosage formulation as disclosed in eg. Remington: The Science and Practice of Pharmacy, 19th Edition (1995) or in Handbook of pharmaceutical granulation technology, chapter 7, "Drugs and the pharmaceutical sciences", vol. 81, 1997; and comprises, but is not limited to, reducing the granulate to a particular size, lubrication, and compressing into tablets or filling into gelatine capsules.

The term "an oral solid dosage formulation" or "an oral solid dosage form" is intended mean such solid dosage formulations as disclosed in eg. Remington: The Science and Practice of Pharmacy, 19th Edition (1995) or in Handbook of pharmaceutical granulation technology, chapter 7, "Drugs and the pharmaceutical sciences", vol. 81, 1997; and comprises, but is not limited to, tablets, incl. chewable tablets, capsules, pills, lozenges, troches, cachets and pellets.

The term "pharmaceutically acceptable salt" represents salt forms of an active ingredient, eg. a compound of formula I, that are physiologically suitable for pharmaceutical use. The pharmaceutically acceptable salts can exist in conjunction with a compound of formula I as acid addition primary, secondary, tertiary, or quaternary ammonium, alkali metal, or alkaline earth metal salts. Generally, the acid addition salts are prepared by the reaction of an acid with an active ingredient, eg. a compound of formula I. The alkali metal and alkaline earth metal salts are generally prepared by the reaction of the metal hydroxide of the desired metal salt with a compound of formula I, wherein R is hydrogen.

Within the present invention, the active ingredient, eg. compounds of formula I may be prepared in the form of a salt such as pharmaceutically acceptable salts, especially acid-addition salts, including salts of organic acids and mineral acids. Examples of such salts include salts of organic acids such as formic acid, fumaric acid, acetic acid, propionic acid, glycolic acid, lactic acid, pyruvic acid, oxalic acid, succinic acid, malic acid, maleic acid, tartaric acid, citric acid, benzoic acid, salicylic acid and the like. Suitable inorganic acid-addition salts include salts of hydrochloric, hydrobromic, sulphuric and phosphoric acids and the like. The acid addition salts may be obtained as the direct products of compound synthesis. In the alternative, the free base may be dissolved in a suitable solvent containing the appropriate acid, and the salt isolated by evaporating the solvent or otherwise separating the salt and solvent.

The term "hydrophilic binder" represents binders commonly used in the formulation of pharmaceuticals, such as polyvinylpyrrolidone, copolyvidone (cross-linked polyvinylpyrrolidone), polyethylene glycol, sucrose, dextrose, corn syrup, polysaccharides (including acacia, tragacanth, guar, and alginates), gelatin, and cellulose derivatives (including hydroxypropyl methylcellulose, hydroxypropyl cellulose, and sodium carboxymethylcellulose).

The term "water-soluble diluent" represents compounds typically used in the formulation of pharmaceuticals, such as sugars (including lactose, sucrose, and dextrose), polysaccharides (including dextrates and maltodextrin), polyols (including mannitol, xylitol, and sorbitol), and cyclodextrins.

The term "non water-soluble diluent" represents compounds typically used in the formulation of pharmaceuticals, such as calcium phosphate, calcium sulfate, starches, modified starches and microcrystalline cellulose.

The term "non water-soluble diluent with non-swelling properties" represents the non water-soluble diluents as indicated above, but excluding starches and modified starches and the like.

The term "surfactant", as used herein, represents ionic and nonionic surfactants or wetting agents commonly used in the formulation of pharmaceuticals, such as ethoxylated castor oil, polyglycolyzed glycerides, acetylated monoglycerides, sorbitan fatty acid esters, poloxamers, polyoxyethylene sorbitan fatty acid esters, polyoxyethylene derivatives, monoglycerides or ethoxylated derivatives thereof, diglycerides or polyoxyethylene derivatives thereof, sodium docusate, sodium laurylsulfate, cholic acid or derivatives thereof, lecithins, alcohols and phospholipids.

The term "antioxidant" represents the three groups of antioxidants, true antioxidants, reducing agents and antoxidant synergists, such as tocopherols, tocopherolesters, alkyl gallates, butylated hydroxyanisole, butylated hydroxytoluene, ascorbic acid, citric acid, edetic acid and its salts, lecithin and tartaric acid.

The term "disintegrant" represents compounds such as starches, clays, celluloses, alginates, gums, cross-linked polymers (such as cross-linked polyvinylpyrrolidone and cross-linked sodium carboxymethylcellulose), sodium starch glycolate, low-substituted hydroxypropyl cellulose, and soy polysaccharides. Preferably, the disintegrant is a modified cellulose gum such as e.g. cross-linked sodium carboxymethylcellulose.

The term "lubricant" represents compounds frequently used as lubricants or glidants in the preparation of pharmaceuticals, such as talc, magnesium stearate, calcium stearate, stearic acid, colloidal silicon dioxide, magnesium carbonate, magnesium oxide, calcium silicate, microcrystalline cellulose, starches, mineral oil, waxes, glyceryl behenate, polyethylene glycol, sodium benzoate, sodium acetate, sodium chloride, sodium laurylsulfate, sodium stearyl fumarate, and hydrogenated vegetable oils. Preferably, the lubricant is magnesium stearate or talc, more preferably magnesium stearate and talc in combination.

In one preferred embodiment of the invention, the hydrophilic binder is gelatin, cellulose derivative, polyvinylpyrrolidone or copolyvidone.

In another preferred embodiment of the invention, the water-soluble diluent is a sugar, a polysaccharide or cyclodextrin.

In another preferred embodiment of the invention, the formulation (granulate or oral solid dosage formulation) further comprises a non water-soluble diluent. In one embodiment thereof the non water-soluble diluent is a non water-soluble diluent with non-swelling properties, preferably microcrystalline cellulose.

In another preferred embodiment of the invention, the formulation further comprises an antioxidant. Preferably the antioxidant is tocopherols and tocopherolesters, such as alpha-tocopherol succinate.

In another preferred embodiment of the invention, the formulation further comprises a surfactant. When the surfactant is present, preferably it is an anionic or nonionic surfactant. Representative surfactants from this preferred group include sodium laurylsulfate, polyglycolyzed glycerides, polyoxyethylene sorbitan fatty acid esters, monoglycerides, diglycerides or glycerol.

In another preferred embodiment of the invention, the formulation further comprises a lubricant(s) and/or a disintegrant.

Certain formulations of the present invention are more preferred. More preferably, the hydrophilic binder is polyvinylpyrrolidone or copolyvidone. More preferably, the water-soluble diluent is a sugar, such as lactose, sucrose, dextrose. More preferably, the surfactant, when present, is a nonionic surfactant, such as polyoxyethylene sorbitan fatty acid esters or glycerol.

Certain formulations of the present invention are most preferred. Most preferably, the hydrophilic binder is copolyvidone. Most preferably, the water-soluble diluent is lactose.

The amount of hydrophilic binder in the pharmaceutical formulation according to the invention is preferably from about 1% to about 25% (w/w), more preferably from about 1% to about 15% (w/w), most preferably from about 2.5% to about 15% (w/w).

The amount of water-soluble diluent in the pharmacutical formulation according to the invention is preferably from about 20% to about 98% (w/w), more preferred from about 20% to about 80% (w/w).

The amount of non water-soluble diluent in the pharmacutical formulation according to the invention is preferably from about 1% to about 50% (w/w), more preferred from about 5% to about 30% (w/w).

The amount of the active ingredient, eg. compound of formula I, in the pharmaceutical formulation according to the invention is preferably from about 0.05% to about 50% (w/w), such as from about 0.1% to about 40% (w/w).

The following formulation examples are illustrative only and are not intended to limit the scope of the invention in any way.

Tablets for this invention are prepared utilizing conventional tabletting techniques. A general method of manufacture involves blending of a compound of formula I, or a salt thereof, the water-soluble diluent, hydrophilic binder and optionally a portion of a disintegrant. This blend is then granulated with an aqueous solution of the hydrophilic binder or an aqueous solution of the hydrophilic binder and surfactant and milled, if necessary. The granules are dried and reduced to a suitable size. Any other ingredients, such as lubricants, (e.g. magnesium stearate) and additional disintegrants, are added to the granules and mixed. This mixture is then compressed into a suitable size and shape using conventional tabletting machines such as a rotary tablet press. The tablets may be film coated by techniques well known in the art.

Capsules for this invention are prepared utilizing conventional methods. A general method of manufacture involves blending of a compound of formula I, or a salt thereof, the water-soluble diluent, a hydrophilic binder, and optionally a portion of a disintegrant. This blend is then granulated with an aqueous solution of the hydrophilic binder or an aqueous solution of the hydrophilic binder and surfactant in water, and milled, if necessary.

The granules are dried and reduced to a suitable size. Any other ingredients, such as a lubricant, are added to the granules and mixed. The resulting mixture is then filled into a suitable size hard-shell gelatin capsule using conventional capsule-filling machines.

The preferred range of pharmaceutical formulation (such as oral solid dosage form, e.g. capsule or tablet) strength may be from about 0.1 mg to about 40 mg of a compound of formula I, more preferred from about 0.25 mg to about 5 mg of a compound of formula I, preferably levormeloxifene.

The preferred range of total mass may be from about 40 mg to about 500 mg depending on the strength of the formulation, more preferred from about 80 mg to about 320 mg.

Tablets and capsules may be prepared using the ingredients and procedures as described below.

The following examples and embodiments are illustrative only and are not intended to limit the scope of the invention in any way.

Experimental Part

During the manufacturing of batches for clinical trial a granulation temperature of >60° C. was obtained. During the stability of these batches an increase in degradation products were observed and the high granulation temperature was suspected.

An investigation of the effect of the granulation temperature was initiated with the following temperature interval:

<0° C., <10° C., 20–25° C., 40–45° C., >70° C. The experiment was carried out in laboratory scale in a high shear mixer of 1 l carried out on a tablet formulation with the following composition. (see formulation 1) After manufacture the tablets were stored in an open container at stress conditions, 60° C.

The preliminary investigation showed that the granulation temperature had an effect on degradation products. At temperatures lower than 20° C. no further improvement in the stability of the levormeloxifene product was seen.

Based on the observation results further investigation was initiated and the results are described in tables 1 and 2.

TABLE 1

Investigation of granulation temperature.
Levormeloxifene 0.25 mg, total mass: 80 mg
Tablets stored at 60° C. in open petri dishes

| Granulation Temperature | Months of Storage | Degradation Products SUM (%) |
|---|---|---|
| 20–25° C. | 0 | 0.68 |
| | 1 | 2.03 |
| | 2 | 3.27 |
| | 3 | 5.12 |
| 40–45° C. | 0 | 0.71 |
| | 1 | 2.63 |
| | 2 | 3.65 |
| | 3 | 6.07 |
| >70° C. | 0 | 0.76 |
| | 1 | 3.29 |
| | 2 | 4.89 |
| | 3 | 7.98 |

TABLE 2

Investigation of granulation temperature.
Levormeloxifene 0.25 mg, total mass: 120 mg
Tablets stored at 60° C. in open petri dishes

| Granulation Temperature | Months of Storage | Degradation Products SUM (%) |
|---|---|---|
| 20–25° C. | 0 | 0.68 |
| | 1 | 2.68 |
| | 2 | 4.42 |
| | 3 | 6.30 |
| 40–45° C. | 0 | 0.78 |
| | 1 | 3.16 |
| | 2 | 4.74 |
| | 3 | 7.75 |
| >70° C. | 0 | 0.81 |
| | 1 | 4.15 |
| | 2 | 6.03 |
| | 3 | 10.41 |

The stability of a levormeloxifene formulation, such as the formulations disclosed in WO 98/23270, can be improved by lowering the process temperature in the high shear mixer, especially the granulation temperature below 40° C. The most optimal temperature interval is 20–25° C.

From the experiments in table 1 and table 2 it may be observed that the stability of a levormeloxifene formulation can be improved by lowering the total mass.

| Formulation 1 | |
|---|---|
| Ingredient | Weight (mg/tablet) |
| Levormeloxifene fumarate corresponding to 1.25 mg base | 1.57 |
| Microcrystalline Cellulose | 48.0 |
| Crosscarmellose Sodium | 25.0 |
| Copolyvidone | 24.0 |
| Lactose | 217 |
| Magnesium Stearate | 1.60 |
| Talc | 3.20 |

The mixture of levormeloxifene fumarate, lactose, microcrystalline cellulose, and a portion of crosscarmellose sodium and copolyvidone is granulated with an aqueous solution of copolyvidone. During granulation cooling is added. The granules are dried, reduced to a suitable size and mixed with magnesium stearate, talc and remaining crosscarmellose sodium. The mixture is compressed into individual tablets yielding a tablet weight of 320 mg. It is possible to manufacture levormeloxifene tablet strengths in the range of 1.25 mg to 40 mg with a total mass in the range of 160 mg to 320 mg.

| Formulation 2 | |
|---|---|
| Ingredient | Weight (mg/tablet) |
| Levormeloxifene fumarate corresponding to 0.25 mg base | 0.314 |
| Microcrystalline Cellulose | 15.5 |
| Crosscarmellose Sodium | 6.00 |
| Copolyvidone | 7.50 |
| Lactose | 69.2 |
| Magnesium Stearate | 0.500 |
| Talc | 1.00 |

The mixture of levormeloxifene fumarate, lactose, microcrystalline cellulose, and a portion of crosscarmellose sodium and copolyvidone is granulated with an aqueous solution of copolyvidone. During granulation cooling is added. The granules are dried, reduced to a suitable size and mixed with magnesium stearate, talc and remaining crosscarmellose sodium. The mixture is compressed into individual tablets yielding a tablet weight with in the range of 80 mg to 160 mg. It is possible to manufacture levormeloxifene tablet strengths in the range of 0.1 mg to 5 mg with a total mass in the range of 80 mg to 160 mg.

In all of the below formulations 3–22 cooling is applied (added) during granulation.

| Formulation 3 | |
|---|---|
| Ingredient | weight (mg/tablet) |
| Levormeloxifene fumarate corresponding to 40 mg base | 50.00 mg |
| Microcrystalline cellulose | 48.00 mg |
| Crosscarmellose sodium | 25.00 mg |
| Copolyvidone | 24.00 mg |
| Na-laurylsulfate | 6.40 mg |
| Lactose | 161.80 mg |
| Magnesium stearate | 1.60 mg |
| Talc | 3.20 mg |

The mixture of levormeloxifene fumarate, lactose, microcrystalline cellulose, and a portion of crosscarmellose sodium and copolyvidone is granulated with an aqueous solution of copolyvidone containing dissolved sodium laurylsulfate. The granules are dried, reduced to a suitable size and mixed with magnesium stearate, talc and remaining crosscarmellose sodium. The mixture is compressed into individual tablets yielding a tablet weight of 320 mg. It is possible to manufacture levormeloxifene tablet strengths in the range of 1.25 mg to 40 mg with a total mass in the range of 160 mg to 320 mg.

| Formulation 4 | |
|---|---|
| Ingredient | weight (mg/tablet) |
| Levormeloxifene fumarate corresponding to 0.25 mg base | 0.314 mg |
| Microcrystalline cellulose | 15.5 mg |
| Crosscarmellose sodium | 6.00 mg |
| Copolyvidone | 7.50 mg |
| Na-laurylsulfate | 2.00 mg |
| Lactose | 67.2 mg |
| Magnesium stearate | 0.50 mg |
| Talc | 1.00 mg |

The mixture of levormeloxifene fumarate, lactose, microcrystalline cellulose, and a portion of crosscarmellose sodium and copolyvidone is granulated with an aqueous solution of copolyvidone containing dissolved sodium laurylsulfate. The granules are dried, reduced to a suitable size and mixed with magnesium stearate, talc and remaining crosscarmellose sodium. The mixture is compressed into individual tablets yielding a tablet weight with in the range of 80 mg to 160 mg. It is possible to manufacture levormeloxifene tablet strengths in the range of 0.1 mg to 5 mg with a total mass with in the range of 80 mg to 160 mg.

| Formulation 5 | |
|---|---|
| Ingredient | Weight (mg/tablet) |
| Levormeloxifene fumarate corresponding to 40 mg base | 50.00 mg |
| Dextrose | 168.20 mg |
| Microcrystalline cellulose | 48.00 mg |
| Crosscarmellose sodium | 25.00 mg |
| Copolyvidone | 24.00 mg |
| Magnesium stearate | 1.60 mg |
| Talc | 3.20 mg |

The mixture of levormeloxifene fumarate, dextrose, microcrystalline cellulose, and a portion of crosscarmellose sodium and copolyvidone is granulated with an aqueous solution of copolyvidone. The granules are dried, reduced to a suitable size and mixed with magnesium stearate, talc and remaining crosscarmellose sodium. The mixture is compressed into individual tablets yielding a tablet weight of 320 mg. It is possible to manufacture levormeloxifene tablet strengths in the range of 1.25 mg to 40 mg with a total mass in the range of 160 mg to 320 mg.

| Formulation 6 | |
|---|---|
| Ingredient | weight (mg/tablet) |
| Levormeloxifene fumarate corresponding to 0.25 mg base | 0.314 mg |

| Formulation 6 -continued | |
|---|---|
| Ingredient | weight (mg/tablet) |
| Dextrose | 69.2 mg |
| Microcrystalline cellulose | 15.5 mg |
| Crosscarmellose sodium | 6.00 mg |
| Copolyvidone | 7.50 mg |
| Magnesium stearate | 0.50 mg |
| Talc | 1.00 mg |

The mixture of levormeloxifene fumarate, dextrose, microcrystalline cellulose, and a portion of crosscarmellose sodium and copolyvidone is granulated with an aqueous solution of copolyvidone. The granules are dried, reduced to a suitable size and mixed with magnesium stearate, talc and remaining crosscarmellose sodium. The mixture is compressed into individual tablets yielding a tablet weight with in the range of 80 mg to 160 mg. It is possible to manufacture levormeloxifene tablet strengths in the range of 0.1 mg to 5 mg with a total mass with in the range of 80 mg to 160 mg.

| Formulation 7 | |
|---|---|
| Ingredient | weight (mg/tablet) |
| Levormeloxifene fumarate corresponding to 40 mg base | 50.00 mg |
| Microcrystalline cellulose | 70.00 mg |
| Crosscarmellose sodium | 31.25 mg |
| Gelatine | 5.00 mg |
| Lactose | 237.75 mg |
| Magnesium stearate | 2.00 mg |
| Talc | 4.00 mg |

The mixture of levormeloxifene fumarate, lactose, microcrystalline cellulose, and a portion of crosscarmellose sodium is granulated with an aqueous solution of gelatine. The granules are dried, reduced to a suitable size and mixed with magnesium stearate, talc and remaining crosscarmellose sodium. The mixture is compressed into individual tablets yielding a tablet weight of 400 mg. It is possible to manufacture levormeloxifene tablet strengths in the range of 1.25 mg to 40 mg with a total mass in the range of 160 mg to 400 mg.

| Formulation 8 | |
|---|---|
| Ingredient | weight (mg/tablet) |
| Levormeloxifene fumarate corresponding to 0.25 mg base | 0.314 mg |
| Microcrystalline cellulose | 15.5 mg |
| Crosscarmellose sodium | 6.00 mg |
| Gelatine | 1.50 mg |
| Lactose | 75.2 mg |
| Magnesium stearate | 0.50 mg |
| Talc | 1.00 mg |

The mixture of levormeloxifene fumarate, lactose, microcrystalline cellulose, and a portion of crosscarmellose sodium is granulated with an aqueous solution of gelatine. The granules are dried, reduced to a suitable size and mixed with magnesium stearate, talc and remaining crosscarmellose sodium. The mixture is compressed into individual tablets yielding a tablet weight with in the range of 80 mg to 160 mg. It is possible to manufacture levormeloxifene tablet strengths in the range of 0.1 mg to 5 mg with a total mass with in the range of 80 mg to 160 mg.

| Formulation 9 | |
|---|---|
| Ingredient | weight (mg/tablet) |
| Levormeloxifene fumarate corresponding to 40 mg base | 50.00 mg |
| Microcrystalline cellulose | 70.00 mg |
| Crosscarmellose sodium | 31.25 mg |
| Dextrose | 237.75 mg |
| Gelatine | 5.00 mg |
| Magnesium stearate | 2.00 mg |
| Talc | 4.00 mg |

The mixture of levormeloxifene fumarate, dextrose, microcrystalline cellulose, and a portion of crosscarmellose sodium is granulated with an aqueous solution of gelatine. The granules are dried, reduced to a suitable size and mixed with magnesium stearate, talc and remaining crosscarmellose sodium. The mixture is compressed into individual tablets yielding a tablet weight of 400 mg. It is possible to manufacture levormeloxifene tablet strengths in the range of 1.25 mg to 40 mg with a total mass in the range of 160 mg to 400 mg.

| Formulation 10 | |
|---|---|
| Ingredient | weight (mg/tablet) |
| Levormeloxifene fumarate corresponding to 0.25 mg base | 0.314 mg |
| Microcrystalline cellulose | 15.5 mg |
| Crosscarmellose sodium | 6.00 mg |
| Dextrose | 75.2 mg |
| Gelatine | 1.50 mg |
| Magnesium stearate | 0.50 mg |
| Talc | 1.00 mg |

The mixture of levormeloxifene fumarate, dextrose, microcrystalline cellulose, and a portion of crosscarmellose sodium is granulated with an aqueous solution of gelatine. The granules are dried, reduced to a suitable size and mixed with magnesium stearate, talc and remaining crosscarmellose sodium. The mixture is compressed into individual tablets yielding a tablet weight with in the range of 80 mg to 160 mg. It is possible to manufacture levormeloxifene tablet strengths in the range of 0.1 mg to 5 mg with a total mass with in the range of 80 mg to 160 mg.

| Formulation 11 | |
|---|---|
| Ingredient | weight (mg/tablet) |
| Levormeloxifene fumarate corresponding to 40 mg base | 50.00 mg |
| Microcrystalline cellulose | 60.00 mg |
| Crosscarmellose sodium | 31.25 mg |
| Copolyvidone | 25.00 mg |
| Tween 80 | 3.25 mg |
| Lactose | 224.50 mg |
| Magnesium stearate | 2.00 mg |
| Talc | 4.00 mg |

The mixture of levormeloxifene fumarate, lactose, microcrystalline cellulose, and a portion of crosscarmellose sodium and copolyvidone is granulated with an aqueous solution of copolyvidone containing Tween 80. The granules are dried, reduced to a suitable size and mixed with magnesium stearate, talc and remaining crosscarmellose sodium. The mixture is compressed into individual tablets yielding a tablet weight of 400 mg. It is possible to manufacture levormeloxifene tablet strengths in the range of 1.25 mg to 40 mg with a total mass in the range of 160 mg to 400 mg.

| Formulation 12 | |
|---|---|
| Ingredient | weight (mg/tablet) |
| Levormeloxifene fumarate corresponding to 0.25 mg base | 0.314 mg |
| Microcrystalline cellulose | 15.5 mg |
| Crosscarmellose sodium | 6.00 mg |
| Copolyvidone | 7.50 mg |
| Tween 80 | 0.80 mg |
| Lactose | 68.4 mg |
| Magnesium stearate | 0.50 mg |
| Talc | 1.00 mg |

The mixture of levormeloxifene fumarate, lactose, microcrystalline cellulose, and a portion of crosscarmellose sodium and copolyvidone is granulated with an aqueous solution of copolyvidone containing Tween 80. The granules are dried, reduced to a suitable size and mixed with magnesium stearate, talc and remaining crosscarmellose sodium. The mixture is compressed into individual tablets yielding a tablet weight with in the range of 80 mg to 160 mg. It is possible to manufacture levormeloxifene tablet strengths in the range of 0.1 mg to 5 mg with a total mass with in the range of 80 mg to 160 mg.

| Formulation 13 | |
|---|---|
| Ingredient | weight (mg/tablet) |
| Levormeloxifene fumarate corresponding to 40 mg base | 50.00 mg |
| Microcrystalline cellulose | 60.00 mg |
| Crosscarmellose sodium | 31.25 mg |
| Copolyvidone | 29.00 mg |
| Glycerol | 3.25 mg |
| Lactose | 220.50 mg |
| Magnesium stearate | 2.00 mg |
| Talc | 4.00 mg |

The mixture of levormeloxifene fumarate, lactose, microcrystalline cellulose, and a portion of crosscarmellose sodium and copolyvidone is granulated with an aqueous solution of copolyvidone containing glycerol. The granules are dried, reduced to a suitable size and mixed with magnesium stearate, talc and remaining crosscarmellose sodium. The mixture is compressed into individual tablets yielding a tablet weight of 400 mg. It is possible to manufacture levormeloxifene tablet strengths in the range of 1.25 mg to 40 mg with a total mass in the range of 160 mg to 400 mg.

| Formulation 14 | |
|---|---|
| Ingredient | weight (mg/tablet) |
| Levormeloxifene fumarate corresponding to 0.25 mg base | 0.314 mg |

-continued

Formulation 14

| Ingredient | weight (mg/tablet) |
| --- | --- |
| Microcrystalline cellulose | 15.5 mg |
| Crosscarmellose sodium | 6.00 mg |
| Copolyvidone | 7.50 mg |
| Glycerol | 0.80 mg |
| Lactose | 68.4 mg |
| Magnesium stearate | 0.50 mg |
| Talc | 1.00 mg |

The mixture of levormeloxifene fumarate, lactose, microcrystalline cellulose, and a portion of crosscarmellose sodium and copolyvidone is granulated with an aqueous solution of copolyvidone containing glycerol. The granules are dried, reduced to a suitable size and mixed with magnesium stearate, talc and remaining crosscarmellose sodium. The mixture is compressed into individual tablets yielding a tablet weight with in the range of 80 mg to 160 mg. It is possible to manufacture levormeloxifene tablet strengths in the range of 0.1 mg to 5 mg with a total mass with in the range of 80 mg to 160 mg.

Formulation 15

| Ingredient | weight (mg/tablet) |
| --- | --- |
| Levormeloxifene fumarate corresponding to 40 mg base | 50.00 mg |
| Microcrystalline cellulose | 68.00 mg |
| Crosscarmellose sodium | 26.25 mg |
| Gelatine | 5.00 mg |
| Glycerol | 6.25 mg |
| Dextrose | 338.50 mg |
| Magnesium stearate | 2.00 mg |
| Talc | 4.00 mg |

The mixture of levormeloxifene fumarate, dextrose, microcrystalline cellulose, and a portion of crosscarmellose sodium is granulated with an aqueous solution of gelatine and glycerol. The granules are dried, reduced to a suitable size and mixed with magnesium stearate, talc and remaining crosscarmellose sodium. The mixture is compressed into individual tablets yielding a tablet weight of 400 mg. It is possible to manufacture levormeloxifene tablet strengths in the range of 1.25 mg to 40 mg with a total mass in the range of 160 mg to 400 mg.

Formulation 16

| Ingredient | weight (mg/tablet) |
| --- | --- |
| Levormeloxifene fumarate corresponding to 0.25 mg base | 0.314 mg |
| Microcrystalline cellulose | 15.5 mg |
| Crosscarmellose sodium | 6.00 mg |
| Gelatine | 1.50 mg |
| Glycerol | 1.50 mg |
| Dextrose | 74.5 mg |
| Magnesium stearate | 0.50 mg |
| Talc | 1.00 mg |

The mixture of levormeloxifene fumarate, dextrose, microcrystalline cellulose, and a portion of crosscarmellose sodium is granulated with an aqueous solution of gelatine and glycerol. The granules are dried, reduced to a suitable size and mixed with magnesium stearate, talc and remaining crosscarmellose sodium. The mixture is compressed into individual tablets yielding a tablet weight with in the range of 80 mg to 160 mg. It is possible to manufacture levormeloxifene tablet strengths in the range of 0.1 mg to 5 mg with a total mass with in the range of 80 mg to 160 mg.

Formulation 17

| Ingredient | weight (mg/tablet) |
| --- | --- |
| Levormeloxifene fumarate corresponding to 40 mg base | 50.00 mg |
| Microcrystalline cellulose | 35.00 mg |
| Crosscarmellose sodium | 26.25 mg |
| hydroxypropyl-betacyclodextrin (HP-cd) | 115.00 mg |
| Gelatine | 5.00 mg |
| Glycerol | 6.25 mg |
| Dextrose | 256.50 mg |
| Magnesium stearate | 2.00 mg |
| Talc | 4.00 |

The mixture of levormeloxifene fumarate, dextrose, hydroxypropyl-betacyclodextrin microcrystalline cellulose, and a portion of crosscarmellose sodium is granulated with an aqueous solution of gelatine containing glycerol. The granules are dried, reduced to a suitable size and mixed with magnesium stearate, talc and remaining crosscarmellose sodium. The mixture is compressed into individual tablets yielding a tablet weight of 500 mg. It is possible to manufacture levormeloxifene tablet strengths in the range of 1.25 mg to 80 mg with a total mass in the range of 160 mg to 500 mg.

Formulation 18

| Ingredient | weight (mg/tablet) |
| --- | --- |
| Levormeloxifene fumarate corresponding to 0.25 mg base | 0.314 mg |
| Microcrystalline cellulose | 15.5 mg |
| Crosscarmellose sodium | 6.00 mg |
| hydroxypropyl-betacyclodextrin (HP-cd) | 28.8 mg |
| Gelatine | 1.50 mg |
| Glycerol | 1.50 mg |
| Dextrose | 45.2 mg |
| Magnesium stearate | 0.50 mg |
| Talc | 1.00 |

The mixture of levormeloxifene fumarate, dextrose, hydroxypropyl-betacyclodextrin microcrystalline cellulose, and a portion of crosscarmellose sodium is granulated with an aqueous solution of gelatine containing glycerol. The granules are dried, reduced to a suitable size and mixed with magnesium stearate, talc and remaining crosscarmellose sodium. The mixture is compressed into individual tablets yielding a tablet weight with in the range of 80 mg to 160 mg. It is possible to manufacture levormeloxifene tablet strengths in the range of 0.1 mg to 5 mg with a total mass with in the range of 80 mg to 160 mg.

Formulation 19 and 20

| Ingredient | Weight |
| --- | --- |
| Levormeloxifene fumarate corresponding to 5 mg base | 6.27 mg |
| Lactose | 395.1 mg |

-continued

Formulation 19 and 20

| Ingredient | Weight |
| --- | --- |
| Microcrystalline cellulose | 9.875 mg |
| Polyvinylpyrrolidone/copolyvidone | 8.400 mg |
| Magnesium stearate | 0.375 mg |

The mixture of levormeloxifene fumarate, lactose and microcrystalline cellulose is granulated with an aqueous solution of polyvinylpyrrolidone or copolyvidone. The granules are dried, reduced to a suitable size and mixed with magnesium stearate. The mixture is then filled into size 0 hard-shell gelatine capsules utilizing conventional encapsulating equipment. In order to obtain different capsule strenghts in the range of 0.18 mg to 7.50 mg, different quantities are weighed out in the range of 15 mg to 500 mg.

Formulation 21

| Ingredient | Weight (mg/tablet) |
| --- | --- |
| Levormeloxifene fumarate corresponding to 0.25 mg base | 0.313 mg |
| Microcrystalline Cellulose | 12.00 mg |
| Crosscarmellose Sodium | 6.25 mg |
| Copolyvidone | 6.00 mg |
| Lactose | 54.20 mg |
| Alpha-tocopherol Succinate | 0.0308 mg |
| Magnesium Stearate | 0.40 mg |
| Talc | 0.80 mg |

The mixture of levormeloxifene fumarate, lactose, microcrystalline cellulose, antioxidant, and a portion of crosscarmellose sodium and copolyvidone is granulated with an aqueous solution of copolyvidone. The granules are dried, reduced to a suitable size and mixed with magnesium stearate, talc and remaining crosscarmellose sodium. The mixture is compressed into individual tablets yielding a tablet weight of 80 mg. It is possible to manufacture levormeloxifene tablet strengths in the range of 0.125 mg to 10 mg with a total mass in the range of 80 mg to 160 mg.

Formulation 22

| Ingredient | Weight (mg/tablet) |
| --- | --- |
| Levormeloxifene fumarate corresponding to 0.25 mg base | 0.314 mg |
| Microcrystalline Cellulose | 15.00 mg |
| Crosscarmellose Sodium | 7.75 mg |
| Copolyvidone | 7.50 mg |
| Lactose | 64.80 mg |
| Alpha-tocopherol Succinate | 0.0308 mg |
| Magnesium Stearate | 0.50 mg |
| Talc | 1.00 mg |

The mixture of levormeloxifene fumarate, lactose, microcrystalline cellulose, antioxidant, and a portion of crosscarmellose sodium and copolyvidone is granulated with an aqueous solution of copolyvidone. The granules are dried, reduced to a suitable size and mixed with magnesium stearate, talc and remaining crosscarmellose sodium. The mixture is compressed into individual tablets yielding a tablet weight of 100 mg. It is possible to manufacture levormeloxifene tablet strengths in the range of 0.125 mg to 20 mg with a total mass of 100 mg.

What is claimed is:

1. A wet granulation method for preparing a granulate the method comprising granulating a mixture containing an active ingredient and a carrier in a high shear mixing means with a temperature regulating means for keeping the temperature below about 40° C. in the mixture during granulation, wherein said active ingredient is a non-peptide organic molecule, small peptide, or peptide mimetic which, when formulated with said carrier and subjected to said high-shear mixing in the absence of said temperature regulation, exhibits increased degradation products relative to a formulation subjected to said high-shear mixing in the presence of said temperature regulation.

2. The method of claim 1 further comprising processing the granulate into an oral solid dosage formulation.

3. A wet granulation method for preparing an oral solid dosage formulation, the method comprising granulating a mixture containing an active ingredient and a carrier, and processing the granulate obtained into an oral solid dosage formulation, wherein the granulation is performed in a high shear mixing means with a temperature regulating means for keeping the temperature below about 40° C. in the mixture during granulation, wherein said active ingredient is a non-peptide organic molecule, small peptide, or peptide mimetic which, when formulated with said carrier and subjected to said high-shear mixing in the absence of said temperature regulation, exhibits increased degradation products relative to a formulation subjected to said high-shear mixing in the presence of said temperature regulation.

4. The method of claim 1, wherein the temperature in the granulation mixture is from about −10° C. to 35° C.

5. The method of claim 1, wherein the active ingredient is a non-peptide organic molecule, small peptide or peptide mimetic selected from the group consisting of centchroman, levormeloxifene, tiagabine, (2E)-5-amino-5-methylhex-2-enoic acid N-methyl-N-((1R)-1-(N-methyl-N-((1R)-1-(methylcarbamoyl)-2-phenylethyl)carbamoyl)-2-(2-naphthyl)ethyl)amide, raloxifene, idoxifene, toremifene, tamoxifene, 4-hydroxy tamoxifene and droloxifene or pharmaceutically acceptable salts thereof.

6. A method for increasing the stability of an active ingredient in a composition subject to high-shear mixing, wherein said active ingredient consists of a compound of formula I

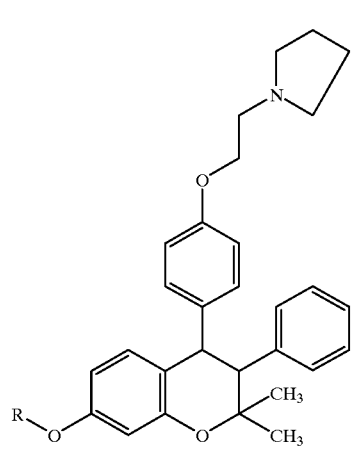

(I)

wherein R is hydrogen or $C_{1-6}$alkyl; or a pharmaceutically acceptable salt thereof, and a carrier, the method comprising:

a) forming a mixture of the compound of formula I and a carrier, b) granulating the mixture, and c) drying the mixture, wherein the granulation is performed in a high shear mixing means with a temperature regulating means for keeping the temperature below about 40° C. in the mixture during granulation.

7. The method of claim 6 further comprising processing the granulate into an oral solid dosage formulation.

8. The method of claim 6 wherein the temperature in the granulation mixture is from about −10° C. to 35° C.

9. The method of claim 6 wherein the compound of formula I is (−)-3R,4R-trans-7-methoxy-2,2-dimethyl-3-phenyl-4-{4-[2-(pyrrolidin-1-yl)ethoxy]phenyl}chromane.

10. The method of claim 1 wherein the carrier comprises a hydrophilic binder and a water-soluble diluent.

* * * * *